United States Patent
Li et al.

(10) Patent No.: US 6,440,263 B1
(45) Date of Patent: Aug. 27, 2002

(54) INDIRECT ENDPOINT DETECTION BY CHEMICAL REACTION AND CHEMILUMINESCENCE

(75) Inventors: Leping Li, Poughkeepsie, NY (US); James Albert Gilhooly, Saint Albans; Clifford Owen Morgan, III, Burlington, both of VT (US); William Joseph Surovic, Carmel; Cong Wei, Poughkeepsie, both of NY (US)

(73) Assignee: International Business Machines Corporation, Armonk, NY (US)

( * ) Notice: Subject to any disclaimer, the term of this patent is extended or adjusted under 35 U.S.C. 154(b) by 53 days.

(21) Appl. No.: 09/641,175

(22) Filed: Aug. 17, 2000

Related U.S. Application Data

(62) Division of application No. 09/073,604, filed on May 6, 1998, now Pat. No. 6,126,848.

(51) Int. Cl.$^7$ .......................... B24B 1/00; H01L 21/302
(52) U.S. Cl. .................... 156/345.12; 216/88
(58) Field of Search ............... 156/345; 216/37, 216/88; 451/66

(56) References Cited

U.S. PATENT DOCUMENTS

| | | | |
|---|---|---|---|
| 3,503,711 A | 3/1970 | Skala | 23/232 |
| 3,882,028 A * | 5/1975 | Zolner | 250/361 C |
| 3,904,371 A * | 9/1975 | Neti et al. | 436/113 |
| 3,963,928 A * | 6/1976 | Zolner | 250/361 |
| 4,268,279 A | 5/1981 | Shindo et al. | |
| 4,328,068 A * | 5/1982 | Curtis | 216/60 |
| 4,333,735 A * | 6/1982 | Hardy et al. | 436/114 |
| 4,493,745 A | 1/1985 | Chen et al. | 156/626 |
| 4,512,964 A | 4/1985 | Vayenas | 423/403 |
| 4,754,089 A * | 6/1988 | Matson et al. | 570/260 |
| 4,812,416 A | 3/1989 | Hewig et al. | 437/5 |
| 4,961,834 A | 10/1990 | Kuhn et al. | 204/412 |
| 4,975,141 A | 12/1990 | Greco et al. | 156/626 |
| 5,234,567 A | 8/1993 | Hobbs et al. | 205/415 |
| 5,242,532 A | 9/1993 | Cain | 156/626 |

(List continued on next page.)

FOREIGN PATENT DOCUMENTS

| | | | |
|---|---|---|---|
| JP | 3277947 | 12/1991 | G01N/21/77 |
| JP | 06-318583 | 11/1994 | |
| JP | 07-221099 | 8/1995 | |
| JP | 08-064561 | 3/1996 | |
| JP | 08-162431 | 6/1996 | |
| WO | WO 9607469 | 3/1996 | |

OTHER PUBLICATIONS

Carr et al., "Endpoint Detection of CMP of Circuitized Multilayer Substrate" IBM Tech. Dis. Bulletin, vol. 34, No. 4B, pp. 406–406, Nov. 1991.*

Biolsi, et al,"An Advanced Endpoint Detection Solution for <1% Open Areas", Solid State Technology, Dec. 1996, pp. 59–67.

(List continued on next page.)

*Primary Examiner*—Gregory Mills
*Assistant Examiner*—Sylvia R. MacArthur
(74) *Attorney, Agent, or Firm*—Jay H. Anderson

(57) ABSTRACT

Detection of the endpoint for removal of a target film overlying a stopping film by removing the target film with a process that selectively generates a chemical reaction product (for example ammonia when polishing a wafer with a nitride film in a slurry containing KOH) with one of the stopping film and the target film, converting the chemical reaction product to a separate product, producing excited molecules from the separate product, and monitoring the level of light emitted from the excited molecules as the target film is removed.

5 Claims, 5 Drawing Sheets

U.S. PATENT DOCUMENTS

| | | | | |
|---|---|---|---|---|
| 5,242,882 A | | 9/1993 | Campbell | 502/325 |
| 5,256,387 A | | 10/1993 | Campbell | 423/392 |
| 5,262,279 A | * | 11/1993 | Tsang et al. | 430/311 |
| 5,395,589 A | | 3/1995 | Nacson | 422/88 |
| 5,399,234 A | | 3/1995 | Yu et al. | 156/636 |
| 5,405,488 A | | 4/1995 | Dimitrelis et al. | 156/627 |
| 5,439,551 A | | 8/1995 | Meikle et al. | 156/626 |
| 5,559,428 A | | 9/1996 | Li et al. | 324/71.5 |
| 5,633,170 A | * | 5/1997 | Neti | 436/116 |
| 5,931,722 A | * | 8/1999 | Ohmi et al. | 451/271 |
| 5,966,586 A | * | 10/1999 | Hao | 438/7 |
| 6,007,408 A | * | 12/1999 | Sandhu | 451/41 |
| 6,296,806 B1 | * | 10/2001 | Kishkovich et al. | 422/52 |

OTHER PUBLICATIONS

Economou, et al, "In Situ Monitoring of Etching Uniformity in Plasma Reactors", Solid State Technology, Apr., 1991, pp. 107–111.

Roland, et al, "Endpoint Detecting in Plasma Etching", J. Vac. Sci. Technol. A3(3), May/Jun. 1985, pp. 631–636.

Park, et al, "Real Time Monitoring of NH, Concentration Using Diffusion Scrubber Sampling Technique and Result of Application to the Processing of Chemically Amplified Resists", Jpn. J. Appl. Phys. vol. 34 (1995) pp. 6770–6773 Part 1 No. 12B, Dec., 1995.

Carr, et al, Technical Disclosure Bulletin, "End–Point Detection of Chemical/Mechanical Polishing of Circuitized Multilayer Substrates", YO887–0456, vol. 34 No. 4B, Sep. 1991 pp. 406–407.

Carr, et al, Technical Disclosure Bulletin, "End–Point Detection of Chemical/Mechanical Polishing of Thin Film Structures", YO886–0830, vol. 34 No. 4A, Sep. 1991, pp. 198–200.

Rutten, Research Diclosure Endpoint Detection Method for Ion Etching of Material Having a Titaniun Nitride Underlayer, BU890–0132, Feb. 1991, No. 322, Kenneth Mason Publications Ltd, England.

* cited by examiner

INDIRECT ENDPOINT DETECTION BY CHEMICAL REACTION AND CHEMILUMINESCENCE

RELATED APPLICATIONS

This application is a divisional application of Ser. No. 09/073,604 filed May 6, 1998 now U.S. Pat. No. 6,126,848

This invention is related to the following copending U.S. Patent applications:

Ser. No. 09/073,605, entitled "Indirect Endpoint Detection by Chemical Reaction";

Ser. No. 09/073,601, Filed May 6, 1998 now U.S. Pat. No. 6,194,230 entitled "Endpoint Detection by Chemical Reaction and Light Scattering";

Ser. No. 09/073,602, Filed May 6, 1998 now U.S. Pat. No. 6,180,422 entitled "Endpoint Detection by Chemical Reaction";

Ser. No. 09/073,607, Filed May 4, 1998 now U.S. Pat. No. 5,959,662 entitled "Endpoint Detection by Chemical Reaction and Reagent"; and Ser. No. 09/073,603, Filed May 6, 1998 now abandoned entitled "Reduction of a Gaseous Product in Solution"; and Ser. No. 09/073,606, Filed May 6, 1998 now U.S. Pat. No. 6,228,769 entitled "Endpoint Detection by Chemical Reaction and Photoionization";

all filed on the same day, all assigned to the present assignee, and all incorporated by reference in their entireties.

FIELD OF THE INVENTION

This invention is directed to semiconductor processing and more particularly to the detection of the endpoint for removal of one film overlying another film.

BACKGROUND OF THE INVENTION

In the semiconductor industry, critical steps in the production of integrated circuits are the selective formation and removal of films on an underlying substrate. The films are made from a variety of substances, and can be conductive (for example metal or a magnetic ferrous conductive material) or non-conductive (for example an insulator). Conductive films are typically used for wiring or wiring connections. Non-conductive or dielectric films are used in several areas, for example as interlevel dielectrics between layers of metallization, or as isolations between adjacent circuit elements.

Typical processing steps involve: (1) depositing a film, (2) patterning areas of the film using lithography and etching, (3) depositing a film which fills the etched areas, and (4) planarizing the structure by etching or chemical-mechanical polishing (CMP). Films are formed on a substrate by a variety of well-known methods, for example physical vapor deposition (PVD) by sputtering or evaporation, chemical vapor deposition (CVD), plasma enhanced chemical vapor deposition (PECVD). Films are removed by any of several well-known methods, for example chemical-mechanical polishing (also known as CMP), dry etching such as reactive ion etching (RIE), wet etching, electrochemical etching, vapor etching, and spray etching.

It is extremely important with removal of films to stop the process when the correct thickness has been removed (the endpoint has been reached). With CMP, a film is selectively removed from a semiconductor wafer by rotating the wafer against a polishing pad (or rotating the pad against the wafer, or both) with a controlled amount of pressure in the presence of a slurry. Overpolishing (removing too much) of a film results in yield loss, and underpolishing (removing too little) requires costly rework (redoing the CMP process). Various methods have been employed to detect when the desired endpoint for removal has been reached, and the polishing should be stopped.

The prior art methods for CMP endpoint detection suitable for all types of films involve the following types of measurement: (1) simple timing, (2) friction by motor current, (3) capacitive, (4) optical, (5) acoustical, and (6) conductive.

An exception to the above is U.S. Pat. No. 5,399,234 to Yu et al, in which a chemical reaction is described between potassium hydroxide in the polishing slurry and the layer being polished. The endpoint for polishing is monitored by sending acoustic waves through the slurry and detecting changes in the acoustic velocity as the concentration of reaction product (thought to be silanol in the case of polishing silicon dioxide) from the layer being polished decreases upon reaching an underlying polish stop layer.

These prior art methods each have inherent disadvantages such as inability for real-time monitoring, the need to remove the wafer from the process apparatus for examining the completion of polishing (not in-situ), or a lack of sensitivity.

These disadvantages have been overcome with an in-situ endpoint detection scheme for conductive films as described in U.S. Pat. No. 5,559,428 to Li et al titled "In-Situ Monitoring of the Change in Thickness of Films," however a suitable endpoint detection for non-conductive films has yet to be described.

Thus, there remains a need for an in-situ, real-time endpoint detection scheme suitable for use with all types of films. Such a scheme should have high detection sensitivity and extremely fast response time, preferably less than 1 or 2 seconds.

SUMMARY OF THE INVENTION

It is therefore an object of the present invention to provide a method and apparatus for detecting the endpoint for removal of any type of film overlying another film.

Another object of the present invention is to provide for in-situ endpoint detection as the film is being removed.

Yet another object is to provide endpoint detection with high detection sensitivity and extremely fast response time.

In accordance with the above listed and other objects, a method for detecting the endpoint for removal of a target film overlying a stopping film, by: (a) removing the target film with a process that selectively generates a chemical reaction product with one of the stopping film and the target film; (b) converting the chemical reaction product to a separate product; (c) producing an excited species from the separate product; and (d) monitoring the level of light emitted from the excited species as the target film is removed is described.

BRIEF DESCRIPTION OF THE DRAWINGS

These and other features, aspects, and advantages will be more readily apparent and better understood from the following detailed description of the invention, in which.

DESCRIPTION OF THE PREFERRED EMBODIMENTS

The present invention is described herein in the context of chemical-mechanical polishing merely as a specific example, and is not meant to limit applicability of the invention to semiconductor technology. Those skilled in the art will understand that the invention is broadly applicable to any process in which it is desirable to detect the endpoint for removal of a target film overlying a stopping film, by (a) removing the target film with a process that selectively generates a chemical reaction product with one of the stopping film and the target film; (b) converting the chemical reaction product to a separate product; (c) producing an excited species from the separate product; and (d) monitoring the level of light emitted from the excited species as the target film is removed.

Figure 1:
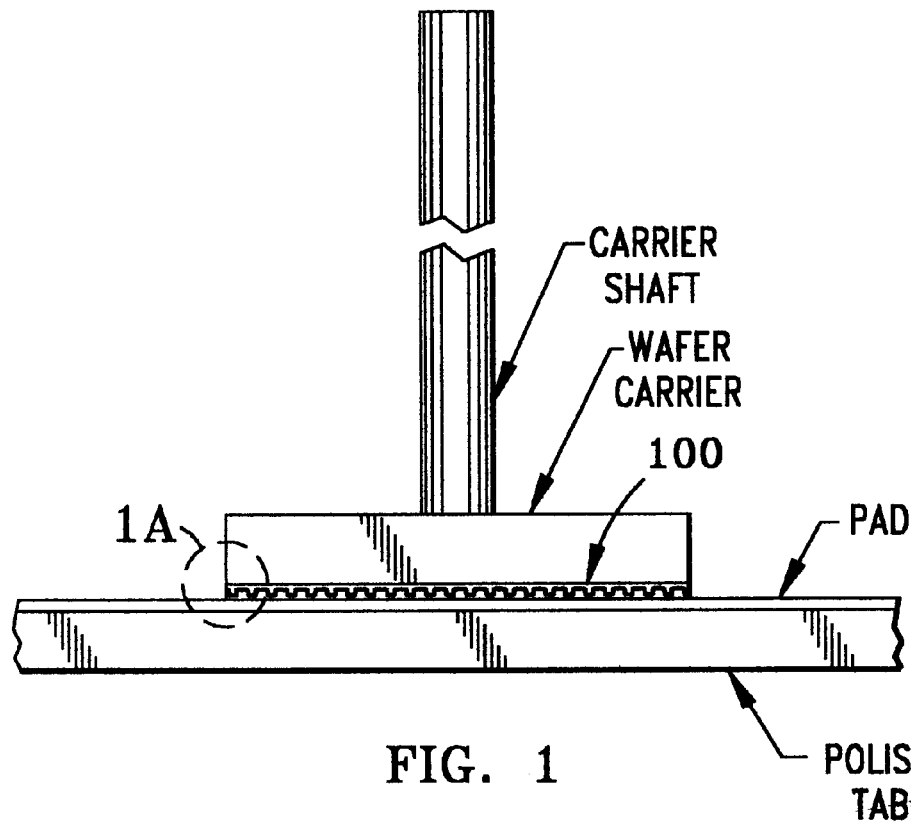
FIG. 1 shows a cross-section of a target film to be chemically-mechanically polished.
Figure 1A:
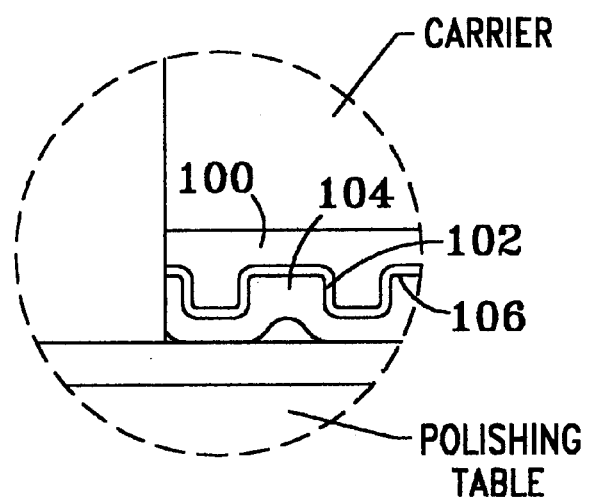

As shown in FIG. 1, we have discovered that when chemically-mechanically polishing a substrate 100 with a target film of oxide ($SiO_2$) 104 over a stopping film of nitride ($Si_3N_4$) 102 with a slurry containing potassium hydroxide (KOH), a chemical reaction occurs when the interface 106 is reached, resulting in the production of ammonia ($NH_3$). More specifically, the slurry used is a mixture of fumed silica, water, and KOH, with a pH of about 10.5. When polishing oxide, the following reaction occurs:

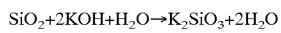

When polishing nitride, the following reaction occurs:

The ammonia produced is dissolved in the slurry, and because of the relatively high pH it exists primarily in the form of $NH_3$ rather than $NH_4^+$. Thus the change in the level of ammonia in the slurry indicates that the underlying nitride film has been reached, and the endpoint for removal of the oxide film can be determined by monitoring the level of ammonia in the slurry. Once the endpoint is reached, the polishing can be stopped.

More generally, the endpoint for removal of any non-nitride-containing film overlying a nitride-containing film can be detected by monitoring the level of ammonia in the slurry. Conversely, the endpoint for removal of a nitride-containing film overlying a non-nitride-containing film can also be detected in a similar manner, with a marked decrease in the presence of ammonia indicating the endpoint.

Even more generally, the endpoint for removal of any film overlying another film can be detected by monitoring the level of a chemical reaction product in the slurry as a component of the slurry reacts selectively with one of the films (either the overlying or underlying film). The reaction described above producing ammonia will be discussed as follows but is not intended to limit the scope of the invention to that particular embodiment. In order to implement the above discovery concerning the production of ammonia in an environment suitable for manufacturing, in-situ (i.e. while the wafer is being polished) slurry collection and sampling is required. Preferably, the collection and sampling provide a rapid response with high sensitivity (to ammonia) and minimizes the effect of interference from other substances in the slurry and in the surrounding air.

Unfortunately, the slurry described above already contains ammonia prior to being used for polishing. The ammonia concentration varies from as low as $5.0 \times 10^{-6}$ M to as high as $5.0 \times 10^{-5}$ M. The ammonia produced in the slurry when polishing a blanket (i.e. uniform) layer of nitride is approximately $1.0 \times 10^{-4}$ M at room temperature; for a typical low pattern factor production wafer having a nitride layer which covers 15% of the wafer area (the rest being oxide), polishing at the interface of the oxide/(oxide+nitride) produces $1.5 \times 10^{-5}$ M. In this case, the desired concentration change will not be able to be distinguished from the fluctuation of the pre-polish ammonia concentration during polishing. Therefore the ammonia concentration prior to polishing this type of wafer must be reduced in order to achieve the desired sensitivity.

Figure 2:
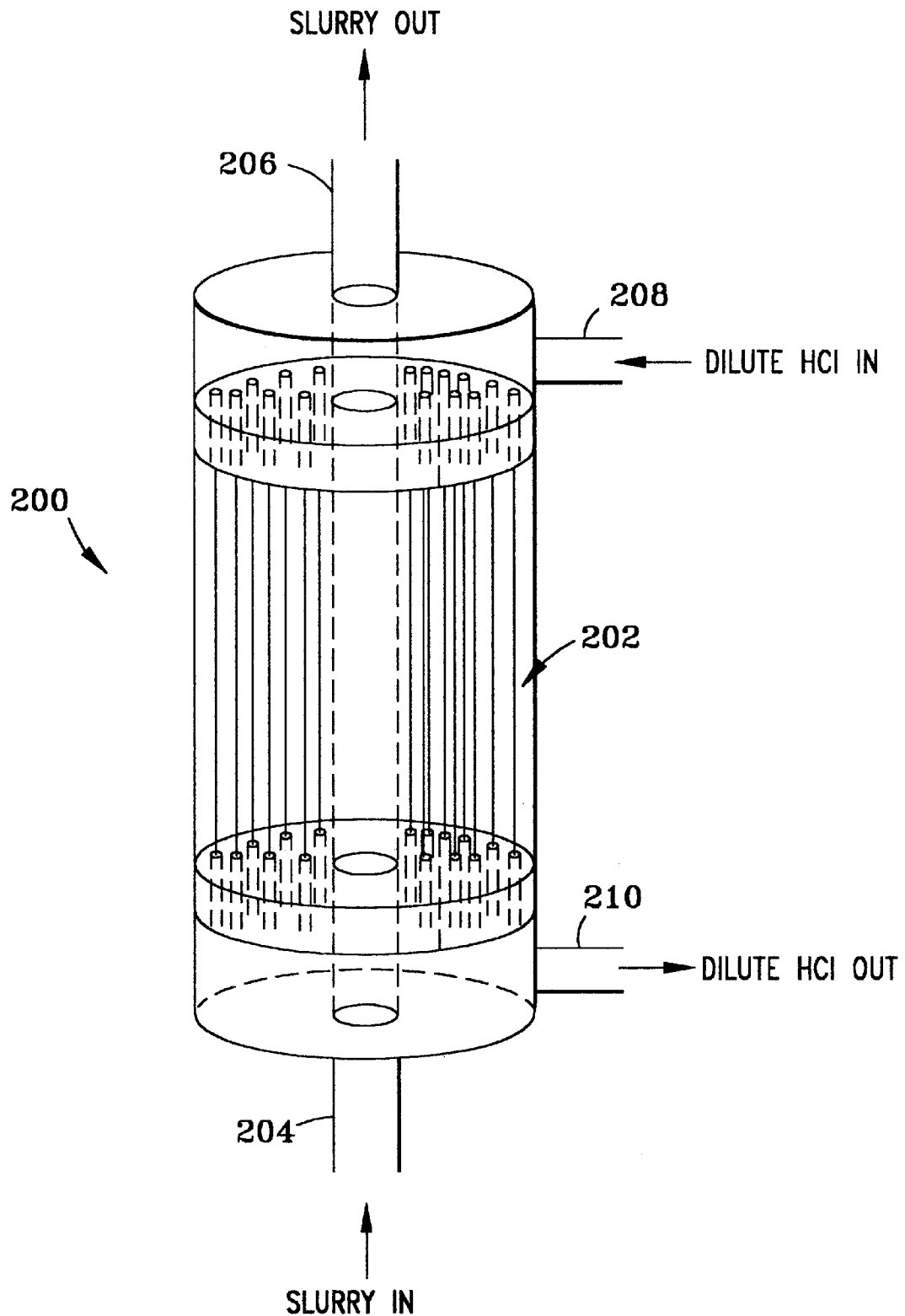
FIG. 2 shows a cross-section of an ammonia scrubber for reducing pre-polish ammonia concentration in the slurry.

The reduction in pre-polish ammonia concentration can be achieved if necessary by using an ammonia scrubber. In the above case, the scrubber reduced the concentration to approximately $2.5 \times 10^{-6}$ M. The main component of the scrubber is a Liqui-Cel Membrane Contactor 200 (model Extra-Flow 4×28 made by Hoechst Celanese) shown in FIG. 2. The Contactor contains Celgard™ microporous polypropylene fibers 202 which are hydrophobic and do not allow water-based solutions to penetrate through the fiber membranes, but do allow gas exchange. Slurry from a reservoir enters contactor 200 at 204 and flows through contactor 200 on the outside of the fibers (also called shellside) allowing ammonia to permeate to the inside of the fibers (also called lumenside) before exiting at 206 and recirculating back to 204. To facilitate removal of the ammonia in the slurry, an aqueous HCl solution from another reservoir with a pH of approximately 3 is circulated in the lumenside, entering at 208 and exiting at 110 before recirculating back to 208. Ammonia gas from the slurry crossing into this HCl stream is immediately converted to $NH_4^+$ by a moderately high concentration of protons, therefore effectively preventing a possible buildup of any appreciable amount of $NH_3$ in the lumenside of the scrubber. The recirculating aqueous HCl stream and reservoir can then be the sink for a large amount of ammonia from the slurry.

With an aqueous HCl reservoir of approximately 10 liters of water adjusted to a pH of 3.5 using 0.1 M HCl solution, and 10 liters of $1.0 \times 10^{-4}$ M ammonia solution at a pH of 10.7 passing through the above-described contactor, the ammonia level was reduced to the desired $2.5 \times 10^{-6}$ M in 30 minutes. The time can be reduced by increasing the size of the contactor, using several contactors in series, or gently heating the slurry to increase the volatility of the ammonia, or any combination of the three. The desired target ammonia level in the slurry can be measured by a commercially available detector such as an ammonia specific ion selective electrode (ISE).

Once the slurry has reached the desired target ammonia level, it is used to polish a wafer. The slurry is then collected from the polishing pad for sampling during the polishing process.

Extraction of Ammonia Gas from the Slurry

Figure 3:
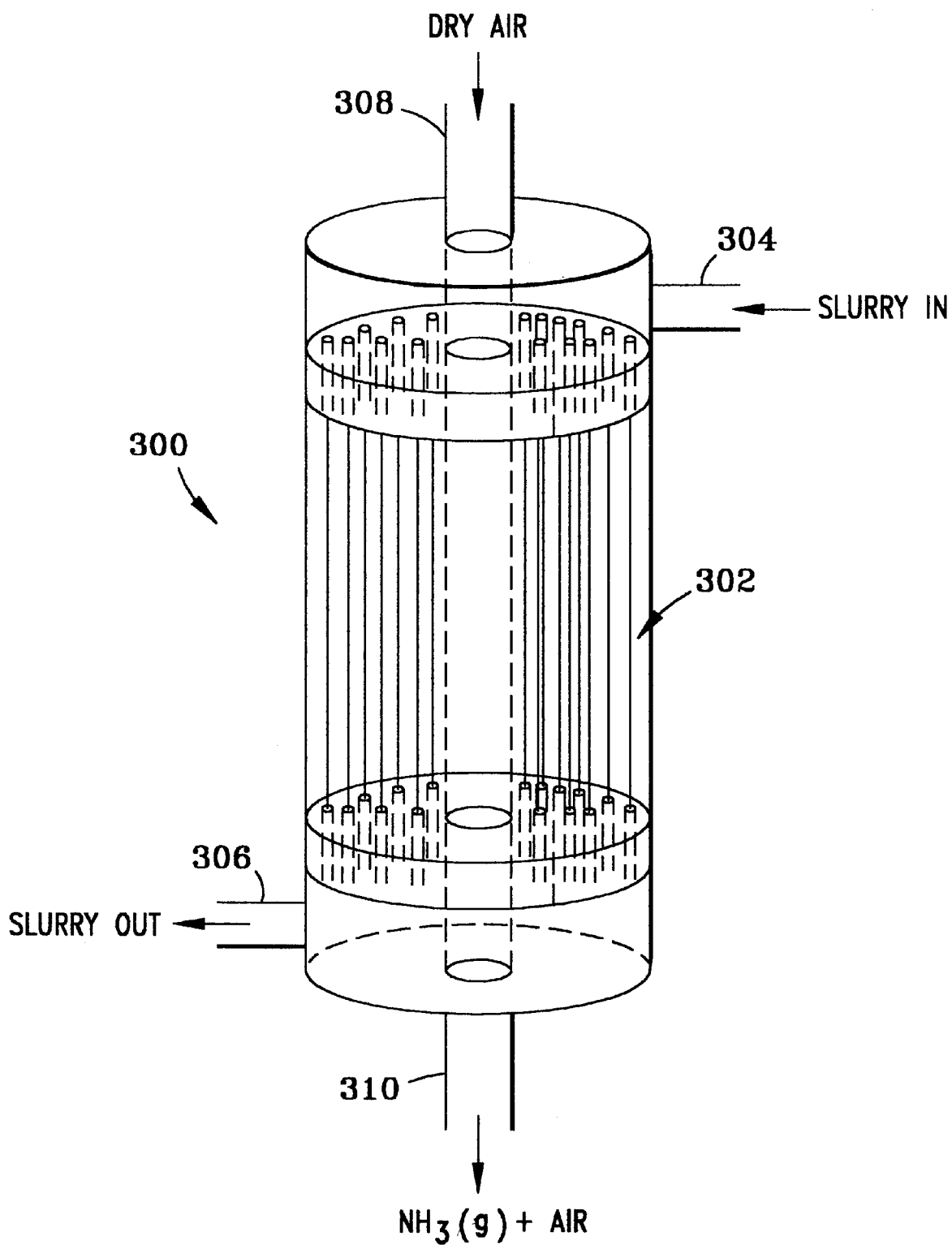
FIG. 3 shows a cross-section of an extraction unit for extracting ammonia gas from the slurry.

In order to detect and monitor ammonia in a gaseous form, thus enabling methods such as mass spectroscopy, slurry from the polishing apparatus (not shown) is pumped through an ammonia extraction unit 300 shown in FIG. 3. Extraction unit 300 is constructed from polypropylene microporous hollow fibers 302 obtained from a dismantled Liqui-Cel Contactor (model 2.5×8 made by Hoechst Celanese). Fibers 302 allow gas but not liquid to pass from the outside to the inside of the fibers.

Slurry is pumped in at 304 through extraction unit 300 on the outside of fibers 302 and exits at 306. Dry and clean gas (from a drier containing an ammonia filter and a deNO$_x$ filter) is pumped in at 308 through the inside of the fibers and exits containing ammonia gas at 310. The carrier gas is pumped at a reduced pressure of approximately 30 Torr 2levelto facilitate ammonia transport from the slurry through the fibers and into the gas stream. The reduced pressure also increases the overall flow velocity, which helps to reduce the response time for measuring the change in ammonia concentration.

The ammonia-containing gas stream from extractor 300 can then be analyzed and monitored for endpoint detection for removal of the target film.

Conversion to Nitric Oxide

Figure 4:
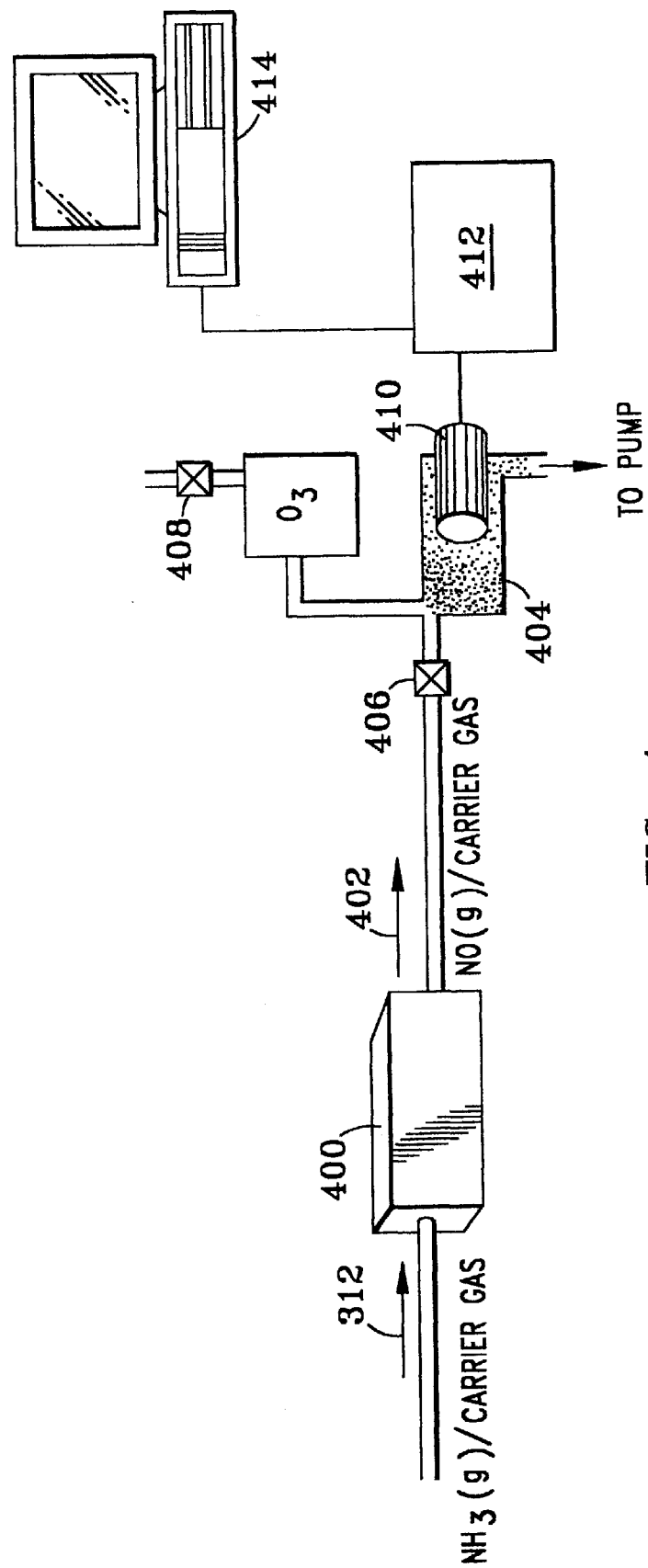
FIG. 4 shows the setup for converting ammonia gas to NO and detection using chemiluminescence.

The ammonia in the ammonia-containing gas stream from the extraction unit 300 (shown in FIG. 3) is converted to a separate product in order to indirectly detect the ammonia by detecting the separate product. An example is converting the ammonia to nitric oxide (NO) using a catalytic converter, as shown in FIG. 4.

Ammonia-containing gas stream 312 enters catalytic converter 400, for example an array of stainless steel tubing having a sufficiently large surface area for a sufficient amount of ammonia molecules to be converted, which is heated to 800 C. The conversion, known as the Oswald process, is described by the reaction $$4NH_3 \text{ (g)} + 5O_2 \text{ (g)} \rightarrow 4NO \text{ (g)} + 6H_2O \text{ (g)}.$$

The carrier gas should be dry and clean so that fast response time as well as a minimum of background NO can be achieved. The conversion to NO plus measurement of the NO by chemiluminescence enables detection at a sub-ppb level as well as avoids interference from other chemicals.

Chemiluminescence Detection (CLD)

The phenomenon of chemiluminescence occurs when an excited molecule, produced from a chemical reaction, emits light in the transition from an excited state to an allowed lower state. Chemiluminescence can be used to detect the presence of ammonia (indirectly by detecting nitric oxide) in this case according to the following:

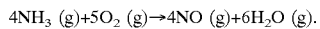

$$NO_2^* \text{ (g)} \rightarrow NO_2 \text{ (g)} + h\nu$$

where the emitted light (photons) are detected by a highly sensitive photomultiplier tube (PMT).

The setup for chemiluminescence detection (CLD) is shown in FIG. 4. NO containing gas stream 402 exiting converter 400 enters a chemiluminescence detector 404 through a flow restrictor 406, and is mixed with ozone in the reaction chamber. The ozone is produced by a conventional ozone generator, with a flow restrictor 408 as shown. In the reaction chamber, NO and $O_3$ react as shown above to produce excited $NO_2^*$ molecules, which emits light in a broad band centered at 1200 nm. A very sensitive PMT 410 (for example a detector from ECO Physics, Zurich, Switzerland) detects the emission through a color filter used to reject photons with undesired wavelengths. PMT 410 is operated in photon counting mode and is controlled and processed by signal conditioner 412. The signal is then fed to a computer 414 which monitors the $NO_2^*$ chemiluminescence signal and controls the polishing process using an output connection to the polishing machine (not shown).

Figure 5:
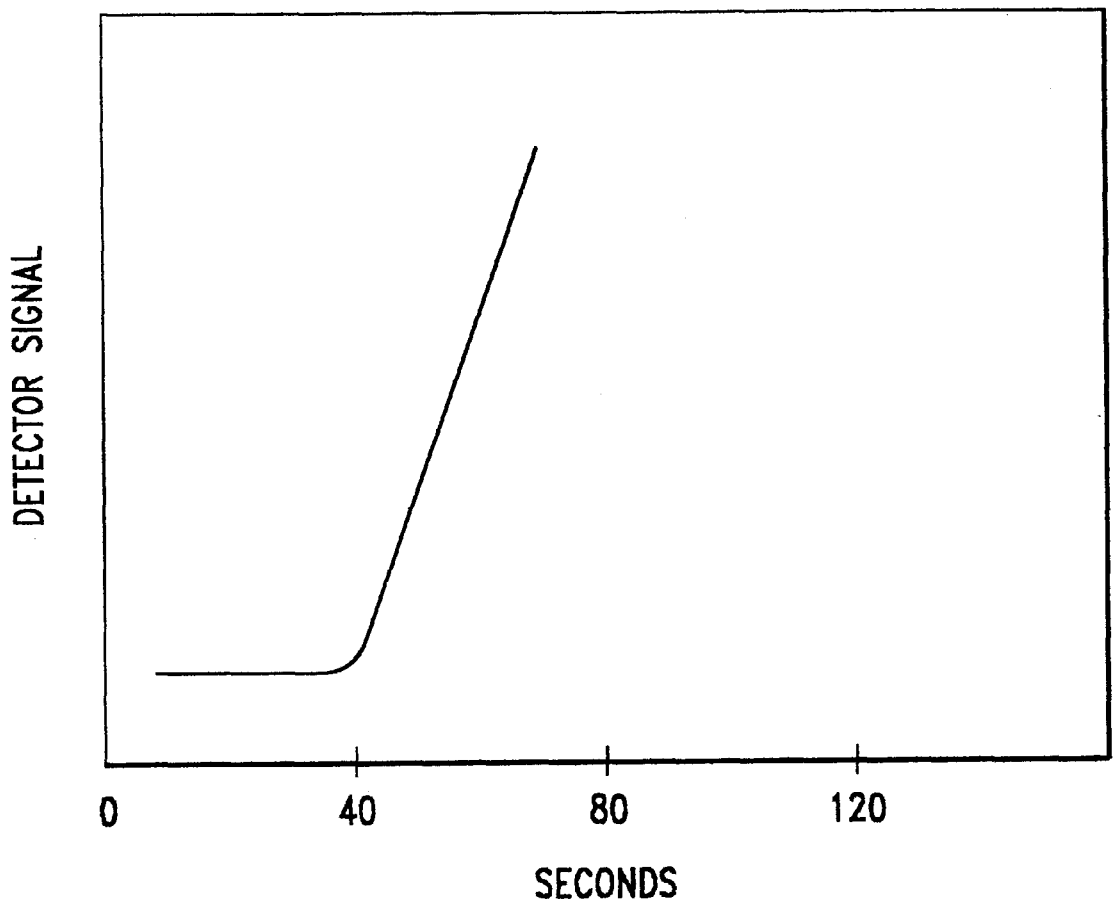
FIG. 5 shows the output trace from the computer monitoring the polishing of a semiconductor wafer; all in accordance with the present invention.

FIG. 5 shows the output from the system used to monitor the polishing of a semiconductor wafer with a layer of oxide ($SiO_2$) over nitride ($Si_3N_4$). The target film being removed is thus the oxide layer, and the stopping film is the nitride layer. Prior to 41 seconds trace 500 corresponds to the polishing of only the oxide, and after 41 seconds the trace indicates that the nitride is being polished, with ammonia being generated. The point at which the nitride polish stop is exposed is very clear, and levels of less than 1 ppb have been detected with a response time of one second or less.

Note that the chemiluminescence method and apparatus described are not restricted to use with monitoring the endpoint for CMP. If an overlying film is being removed from an underlying film by etching, for example dry etching (e.g. reactive ion etching), an underlying film (i.e. etch stop) may be selected which generates a marker chemical reaction product upon contact with the etchants. The reaction products of the etching process can be sampled by this method in order to monitor the level of the marker chemical reaction product.

In summary, a method and associated apparatus have been described which are capable of detecting the endpoint for removal of any type of film overlying another film. The present invention provides for in-situ endpoint detection as the film is being removed, and with high detection sensitivity and extremely fast response time.

While the invention has been described in terms of specific embodiments, it is evident in view of the foregoing description that numerous alternatives, modifications and variations will be apparent to those skilled in the art. Thus, the invention is intended to encompass all such alternatives, modifications and variations which fall within the scope and spirit of the invention and the appended claims.

What is claimed is:

1. An apparatus for detecting the endpoint for removal of a target film overlying a stopping film by a chemical-mechanical polishing process using a polishing slurry, the apparatus comprising:

an extractor for extracting a chemical reaction product as a gas from the slurry, the chemical reaction product being selectively generated in a chemical reaction with one of the stopping film and the target film and dissolved in the slurry during the process;

a converter for converting the chemical reaction product to a separate product;

means for producing excited molecules from the separate product; and a monitor for monitoring the level of light emitted from the excited molecules as the target film is removed.

2. The apparatus of claim 1 wherein the converter comprises a catalytic converter.

3. The apparatus of claim 1 wherein the monitor comprises a photomultiplier.

4. The apparatus of claim 1 wherein the extractor comprises:

means for contacting a first side of a hydrophobic membrane with the slurry;

means for contacting a second side of the hydrophobic membrane with a gas stream; and means for allowing the chemical reaction product to pass through the membrane as a gas and become entrained in the gas stream.

5. The apparatus of claim 1 further comprising means for stopping the removal process when the endpoint has been reached.

* * * * *